United States Patent
Daerr et al.

(10) Patent No.: US 10,281,596 B2
(45) Date of Patent: May 7, 2019

(54) CORRECTING PHOTON COUNTS IN A PHOTON COUNTING X-RAY RADIATION DETECTION SYSTEM

(71) Applicant: KONINKLIJKE PHILIPS N.V., Eindhoven (NL)

(72) Inventors: Heiner Daerr, Hamburg (DE); Axel Thran, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/756,611

(22) PCT Filed: Sep. 9, 2016

(86) PCT No.: PCT/EP2016/071243
§ 371 (c)(1),
(2) Date: Mar. 1, 2018

(87) PCT Pub. No.: WO2017/046002
PCT Pub. Date: Mar. 23, 2017

(65) Prior Publication Data
US 2018/0188391 A1    Jul. 5, 2018

(30) Foreign Application Priority Data
Sep. 18, 2015   (EP) .................................... 15185870

(51) Int. Cl.
*G01T 1/24*   (2006.01)
*A61B 6/03*   (2006.01)
(Continued)

(52) U.S. Cl.
CPC ................ *G01T 1/24* (2013.01); *A61B 6/032* (2013.01); *A61B 6/4241* (2013.01); *G01T 1/29* (2013.01)

(58) Field of Classification Search
CPC .. G01T 1/24; G01T 1/29; A61B 6/032; A61B 6/4241
See application file for complete search history.

(56) References Cited

U.S. PATENT DOCUMENTS 4,937,452 A * 6/1990 Simpson .................. G01T 1/24
  250/370.01
6,331,705 B1 * 12/2001 Eisen ................ H01L 27/14658
  250/370.01
(Continued)

FOREIGN PATENT DOCUMENTS

| WO | 2008/013663 | 1/2008 |
| WO | 2014091278 | 6/2014 |
| WO | 2015/078753 | 6/2015 |

OTHER PUBLICATIONS

Ding, et al., "Image-based spectral distortion correction for photon-counting x-ray detectors"; Medical Physics, vol. 39, No. 4, Apr. 1, 2012.
(Continued)

*Primary Examiner* — Marcus H Taningco

(57) ABSTRACT

The invention relates to a photon counting x-ray radiation detection system. The system (31) comprises an x-ray radiation device (2) for providing polychromatic x-ray radiation (4) for traversing an examination zone (5) during a detection period of a scan. A photon counting detection device (6) comprising detection elements (3) detects the x-ray radiation after having traversed the examination zone and measures for each detection element photon counts in one or more energy bins during the detection period. A correction unit (12) estimates for each detection element an amount of a build up charge present in the detection element and corrects the measured photon counts for the detection element based on the estimated amount of the build up charge. This allows the corruption of the photon count rates caused by the build
(Continued)

up charges to be compensated and to improve the determination of the photon counts.

14 Claims, 4 Drawing Sheets

(51) Int. Cl.
    *A61B 6/00*     (2006.01)
    *G01T 1/29*     (2006.01)

(56) References Cited

U.S. PATENT DOCUMENTS

| | | |
|---|---|---|
| 8,063,378 B2 | 11/2011 | Bolotnikov |
| 2008/0023638 A1 | 1/2008 | Starman |
| 2008/0240366 A1 | 10/2008 | Bacher |
| 2010/0172467 A1* | 7/2010 | Steadman Booker .... G01T 1/17 378/19 |
| 2012/0138808 A1 | 6/2012 | Jung |
| 2014/0233693 A1 | 8/2014 | Wang |
| 2016/0216381 A1* | 7/2016 | Nishihara ............. G01T 1/1644 |
| 2017/0105688 A1* | 4/2017 | Konno ................... A61B 6/032 |

OTHER PUBLICATIONS

Bale, et al., "Electron transport and charge induction in cadmium zinc telluride detectors with space charge build up under intense x-ray irradiation", Journal of Applied Physics, vol. 107, No. 11 (2010).

Alvarez, "Estimator for photon counting energy selective x-ray imaging with multibin pulse height analysis", Medical Physics, vol. 38, No. 5 (2011).

Schlomka et al., "Experimental feasibility of multi-energy photon-counting K-edge imaging in pre-clinical computed tomography", Physics in Medicine and Biology, vol. 53, No. 15 (2008).

Steadman et al., "ChromAIX: Fast photon-counting ASIC for Spectral Computed Tomography", Nuclear Instruments and Methods in Physics Research Section A: Accelerators, Spectrometers, Detectors and Associated Equipment, vol. 648, Suppl. 1 (2011).

* cited by examiner

CORRECTING PHOTON COUNTS IN A PHOTON COUNTING X-RAY RADIATION DETECTION SYSTEM

CROSS REFERENCE TO RELATED APPLICATIONS

This application is the U.S. National Phase application under 35 U.S.C. § 371 of International Application No. PCT/EP2016/071243, filed Sep. 9, 2016, published as WO 2017/046002 on Mar. 23, 2017, which claims the benefit of European Patent Application Number 15185870.1 filed Sep. 18, 2015. These applications are hereby incorporated by reference herein.

FIELD OF THE INVENTION

The invention relates to a photon counting x-ray radiation detection system and method. The invention relates further to a computer program for controlling the photon counting x-ray radiation detection system as well as to an x-ray imaging system comprising the photon counting x-ray radiation detection system.

BACKGROUND OF THE INVENTION

Radiation detectors used for imaging applications like spectrally resolving computed tomography (CT) make use of a direct conversion material, such as cadmium telluride (CdTe), cadmium zinc telluride (CaZnTe) or silicon (Si), that is disposed between a cathode and an anode, with a voltage applied across the cathode and the anode. X-ray photons that illuminate the cathode transfer energy to electrons in the direct conversion material, which creates electron/hole pairs with the electrons drifting towards the anode. The anode, in response, produces an electrical signal that is further processed in order to measure photon counts in one or more energy bins. This is usually done by means of an amplifier which amplifies the electrical signal, a pulse shaper which processes the amplified electrical signal and produces a pulse having a peak amplitude or height that is indicative of the energy of the detected radiation, an energy discriminator which compares the height of the pulse with one or more thresholds, a counter which counts for each threshold the number of times the leading edge of a pulse crosses the threshold, and an energy binner which bins the photon counts into energy ranges, thereby spectrally resolving the detected radiation. The energy binner can, in principle, be implemented in hardware; more typically, however, it is realized by an external software component that reads-in the photon counts from the counter.

D. S. Bale and C. Szeles, "Electron transport and charge induction in cadmium zinc telluride detectors with space charge build up under intense x-ray irradiation", Journal of Applied Physics, Vol. 107, No. 11 (2010) describe that wide band gap semiconductor radiation detectors using a direct conversion material are susceptible to a time dependent positive or negative charge build up that increases under x-ray illumination.

Due to this trapped and time dependent charge (which can be a positive or a negative charge), the amount of x-ray generated electrons is reduced during travel to the anode. Thus, the detected pulse height for a given x-ray energy changes leading to a time dependent photon count rate for a given threshold. This time instability can be very degrading to the quality of generated images, for instance, it can lead to ring artifacts in the images with time dependent strength.

H. Ding and S. Molloi, "Image-based spectral distortion correction for photon-counting x-ray detectors", Medical Physics, Vol. 39, No. 4 (2012) discloses an image-based spectral distortion correction for photon-counting x-ray detectors. The authors performed experiments where they calibrated a Cadmium-Zinc-Telluride (CZT) photon-counting detector with five energy thresholds using BR12 phantoms of various thicknesses. The measured counts were compared with simulation results and for each ith energy bin a calibration function was derived which translates the measured counts into simulated ones.

WO 2008/013663 A2 discloses a gain/lag artifact correction algorithm and software. A total number of traps to be filled in a detector of an imaging system is estimated based on a measured signal sensed by the detector. The measured signal is adjusted based on the estimated total number of traps and a current trap state of the detector. The trap state of the detector is subsequently updated.

SUMMARY OF THE INVENTION

It is an object of the invention to provide a photon counting x-ray radiation detection system and method, which allows to improve the determination of the photon counts. It is a further object of the invention to provide a computer program for controlling the photon counting x-ray radiation detection system as well as to provide an x-ray imaging system comprising the photon counting x-ray radiation detection system.

In a first aspect of the invention, a photon counting x-ray radiation detection system is presented, wherein the system comprises:

- an x-ray radiation device for providing polychromatic x-ray radiation for traversing an examination zone during a detection period of a scan, wherein the examination zone is adapted to accommodate an object,
- a photon counting detection device comprising detection elements for detecting the x-ray radiation after having traversed the examination zone, wherein the photon counting detection device is adapted to measure for each detection element photon counts in one or more energy bins during the detection period, and
- a correction unit for estimating for each detection element an amount of a build up charge present in the detection element and for correcting the measured photon counts for the detection element based on the estimated amount of the build up charge.

Since the correction unit estimates for each detection element an amount of a build up charge present in the detection element and since it corrects the measured photon counts for the detection element based on the estimated amount of the build up charge, the corruption of the photon count rates caused by the build up charges can be compensated such that the number of photons of the polychromatic x-ray radiation illuminating each detection element in the one or more, for instance, two, three, four, five, six or more, energy bins can be determined more precisely. If the photon counting x-ray radiation detection system is used, for instance, in a spectrally resolving computed tomography system, this improvement in the determination of the photon counts can lead to an improved quality of the generated images.

In an embodiment, the radiation device comprises an x-ray radiation source for emitting the polychromatic x-ray radiation and a collimator for collimating the emitted x-ray radiation into a conical x-ray radiation beam. In another embodiment, the collimator can be adapted to collimate the x-ray radiation into a beam with another shape, for instance, into a fan shape beam.

The detection elements of the photon counting detection device preferably comprise a direct conversion material, such as CdTe, CaZnTe or Si, that is disposed between a cathode and an anode, with a voltage applied across the cathode and the anode. Photons of the polychromatic radiation that illuminate the cathode transfer energy to electrons in the direct conversion material, which creates electron/hole pairs with the electrons drifting towards the anode. The anode, in response, produces an electrical signal that is further processed in order to measure photon counts in the one or more energy bins. To this end, each detection element preferentially comprises an amplifier which amplifies the electrical signal, a pulse shaper which processes the amplified electrical signal and produces a pulse having a peak amplitude or height that is indicative of the energy of the detected radiation, an energy discriminator which compares the height of the pulse with one or more thresholds, and a counter which counts for each threshold the number of times the leading edge of a pulse crosses the threshold. An additional energy binner which bins the photon counts into energy ranges, thereby spectrally resolving the detected radiation, is preferably realized by an external software component that reads-in the photon counts from the counter of each detection element.

It is preferred that the correction unit is adapted to perform the estimating and the correcting for the detection element based on a mathematical correction model having a plurality of model parameters, wherein the correction model models the amount of the build up charge in dependence of time and relates it to correction values for correcting the measured photon count in each energy bin. By making use of such a correction model, the amount of the build up charge that is present in the detection element at a given point in time can be determined. Moreover, since the corruption of the photon count rates is caused by the build up charges, the amount of the build up charge that is present in the detection element can be related to correction values for correcting the measured photon count in each energy bin.

It is further preferred that the modeling of the amount of the build up charge in dependence of time comprises an increase component and a decrease component which respectively model an increase and a decrease of the amount of the build up charge in dependence of time. This allows to take into account the two opposite effects that affect the amount of the build up charge that is present in the detection element at a given point in time: The effect that, on the one hand, the amount of the build up charge increases in dependence of time if the detection element is illuminated with the polychromatic x-ray radiation, and the effect that, on the other hand, the amount of the build up charge decreases in dependence of time due to trapped charges becoming untrapped, e.g., through acoustic phonons, over time, while the state of the material comprised by the detection element relaxes towards an equilibrium state.

More specifically, the increase component preferably depends on a first model parameter which depends on the x-ray radiation and on a material combination of the object on a path of the x-ray radiation from the x-ray radiation device to the detection element. The characteristics of these elements, i.e., the provided polychromatic x-ray radiation and the combination of the materials that the x-ray radiation traverses on its path from the x-ray radiation device to the detection element, determine the spectral distribution of the x-ray radiation that ultimately illuminates the detection element, wherein the respective increase of the amount of the build up charge in the detection element depends on the illumination.

The material combination of the object on the path of the x-ray radiation from the x-ray radiation device to the detection element can be determined, for instance, by comparing the measured photon counts with interpolated calibration photon counts measured for the detection element in the one or more energy bins during a plurality of detection periods of one or more calibration scans, during which a calibration phantom is used as the object. Such a calibration is described in more detail, for instance, in R. E. Alvarez, "Estimator for photon counting energy selective x-ray imaging with multibin pulse height analysis", Medical Physics, Vol. 38, No. 5 (2011), the contents of which are herein incorporated by reference in their entirety.

Preferentially, the decrease component depends on a second model parameter which defines a constant decrease rate of the amount of the build up charge. A constant decrease rate is well suited for modeling the above-described decrease of the amount of the build up charge due to trapped charges becoming untapped, e.g., through acoustic phonons, over time, while the state of the material comprised by the detection element relaxes towards an equilibrium state.

It is preferred that the amount of the build up charge is related to the correction values by a third model parameter which is specific for each energy bin and which depends on a material combination of the object on a path of the x-ray radiation from the x-ray radiation device to the detection element. This third model parameter is an empirical model parameter which preferably describes the proportionality of the amount of build up charge and the change of measured photon counts. The change of the measured photon count in each energy bin depends on the spectral distribution of the x-ray radiation that ultimately illuminates the detection element. This is included in the dependency of the material combination of the third model parameter, since the spectrum of the x-ray radiation impinging on the detector element depends on the amount/combination of the materials the x-ray radiation has traversed on its path from the x-ray radiation device to the detection element.

Preferentially, the modeling of the amount of the build up charge in dependence of time is based on an integration or a summation of amounts of the charge build up (including its decay by de-trapping) during previous detection periods of the scan. By doing so, the changes of the amount of the build up charge that is present in the detection element can be traced over time. Therewith, an estimation of the amount of the build up charge that is present in the detection element can be performed for any given point in time that is reached during the scan, taking into account the 'illumination history' during the scan.

It is context, it is particularly preferred that the integration or summation begins at a first detection period of the scan. By beginning the integration or summation at the first detection period of the scan, the changes of the amount of the build up charge that is present in the detection element can be traced over the whole scan beginning at a well-defined state at which the detection element has not yet been illuminated during the scan.

It is further preferred that the amount of the build up charge is modeled to be equal to a predetermined value, in particular, zero, at the beginning of the first detection period of the scan. For longer idle times between scans, modeling the amount of the build up charge to be equal to zero at the beginning of the first detection period of the scan is considered to be a realistic assumption in view of the fact that the detection element has not yet been illuminated during the (present) scan and that the decrease component of the correction model has most likely decreased substantially any build up charge that may have been present in the detection element due to an illumination during a previous scan to zero during the idle time between the previous scan and the (present) scan. For shorter idle times between scans, another predetermined value may be better suited for modeling the amount of the build up charge at the beginning of the first detection period of the scan. This predetermined value may be determined, for instance, from the estimated amount of the build up charge at the end of a previous scan and the idle time between the previous scan and the (present) scan.

It is preferred that the photon counting x-ray radiation detection system further comprises:

a model parameter determining unit for determining for each detection element the model parameters of the correction model based on calibration photon counts measured for the detection element in the one or more energy bins during a plurality of detection periods of one or more calibration scans, during which a calibration phantom is used as the object.

Depending on the time stability of the photon counting x-ray radiation detection system, the calibration may be performed repeatedly, for instance, on a daily or weekly basis.

It is particularly preferred that the calibration photon counts for the detection element comprise calibration photon counts for different material combinations of the calibration phantom, wherein the model parameter determining unit is adapted to determine the model parameters for the detection element for each of the different material combinations.

The calibration phantom can preferentially comprise several slabs with accurately known dimensions and made of materials whose chemical composition spans the range of atomic numbers of materials expected in the object, such as a human or an animal. For instance, the calibration phantom can comprise a water equivalent material, such as Delrin, only, or it can comprise at least one further material, for instance, a bone equivalent material, such as aluminum, and/or a contrast agent equivalent material, such as iodine. The maximum lengths of the slabs are preferably chosen to span the expected attenuation of the object. The calibration phantom can be placed between the x-ray radiation device and the photon counting detection device and measurements can be made using the same type of scan, e.g. the same scan protocol, as used when scanning the object. If the photon counting x-ray radiation detection system is used, for instance, in a spectrally resolving computed tomography system, the support (gantry) can be fixed to make measurements of the calibration phantom. In order to allow the calibration of each detection element, it is preferred that the slabs of the calibration phantom are constructed wide enough to be simultaneously placed between the x-ray radiation device and each detection element of the photon counting detection device. From the known geometry of the x-ray radiation device, in particular, the shape of the provided x-ray radiation beam, and the photon counting detection device, together with the known dimensions and placement of the slabs of the calibration phantom, the respective material lengths, i.e., the lengths traversed by the x-ray radiation through a respective material from the x-ray radiation device to each of the detection elements can then be determined. Further details regarding a suitable calibration phantom can be found, for instance, in R. E. Alvarez, "Estimator for photon counting energy selective x-ray imaging with multibin pulse height analysis", Medical Physics, Vol. 38, No. 5 (2011), the contents of which are herein incorporated by reference in their entirety.

It is also preferred that the model parameter determining unit is adapted to determine the model parameters for the detection element by fitting the correction model to the calibration photon counts. This allows for a robust and effective way of determining the model parameters.

In another aspect of the invention, an x-ray imaging system is presented, wherein the system comprises:

a photon counting x-ray radiation detection system as defined in claim 1, and a reconstruction unit for reconstructing an image based on the corrected photon counts.

In an embodiment, the x-ray imaging system can be a spectrally resolving computed tomography system for generating an image of an object. The system may be usable, for instance, in medical or dental applications on human or animals, it may be usable in security applications, such as in baggage scanners or hand-held scanners, or in industrial material testing and inspection applications.

In a further aspect of the invention, a photon counting x-ray radiation detection method is presented, wherein the method comprises:

providing polychromatic x-ray radiation for traversing an examination zone during a detection period of a scan, by an x-ray radiation device, wherein the examination zone is adapted to accommodate an object, detecting the x-ray radiation after having traversed the examination zone, by a photon counting detection device comprising detection elements, wherein the photon counting detection device measures for each detection element photon counts in one or more energy bins during the detection period, and estimating for each detection element an amount of a build up charge present in the detection element and correcting the measured photon counts for the detection element based on the estimated amount of the build up charge, by a correction unit.

In another aspect of the invention, a computer program for controlling a photon counting x-ray radiation detection system is presented, wherein the computer program comprises program code means for causing the system to carry out the photon counting x-ray radiation detection method, when the computer program is run on the system.

It shall be understood that the photon counting x-ray radiation detection system of claim 1, the x-ray imaging system, the photon counting x-ray radiation detection method, and the computer program have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
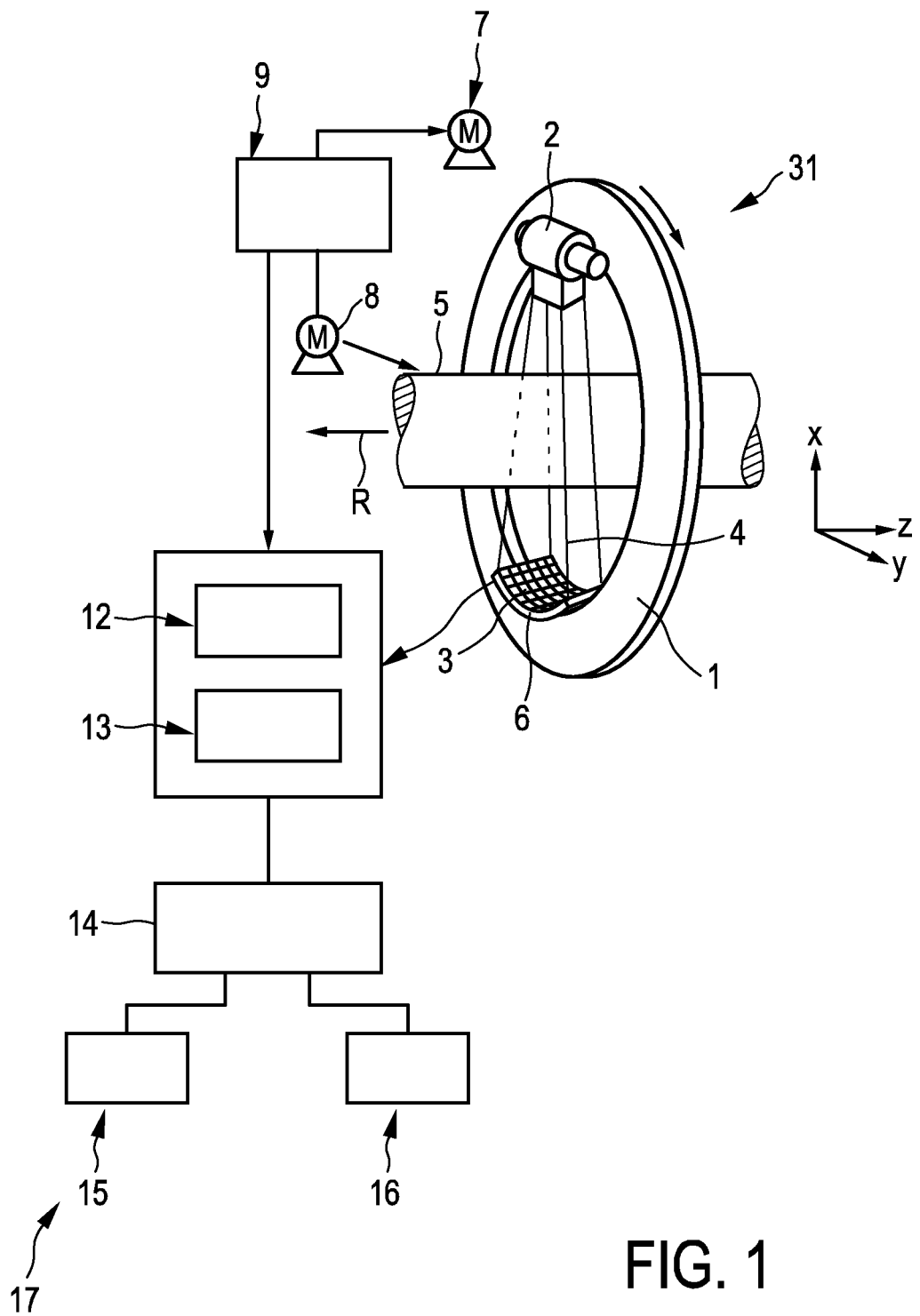
FIG. 1 shows schematically and exemplarily an embodiment of an x-ray imaging system.

FIG. 1 shows schematically and exemplarily an embodiment of an x-ray imaging system, here, a spectrally resolving computed tomography system for generating an image of an object. The spectrally resolving computed tomography system 17 includes a support 1 which is capable of rotating about a rotational axis R which extends parallel to the z direction. An x-ray radiation device 2, which comprises an x-ray tube and which is adapted to provide polychromatic x-ray radiation 4 for traversing an examination zone 5 of the spectrally resolving computed tomography system 17 during a detection period of a scan, is mounted on the support 1. In this embodiment, the x-ray radiation device 2 is adapted to provide a conical x-ray radiation beam 4 as the polychromatic x-ray radiation. In another embodiment, the x-ray radiation device 2 can be adapted to provide the polychromatic x-ray radiation with another beam shape, for instance, with a fan beam shape. The x-ray radiation 4 traverses an object (not shown), such as a patient, that is accommodated in the examination zone 5, which is cylindrical in this embodiment. After having traversed the examination zone 5, the x-ray radiation beam 4 is incident on a photon counting detection device 6, which comprises detection elements 3 arranged, here, in a two-dimensional detection surface. The photon counting detection device 6 is mounted on the support 1.

The spectrally resolving computed tomography system 17 comprises two motors 7, 8. The support 1 is driven at a preferably constant but adjustable angular speed by the motor 7. The motor 8 is provided for displacing the object, for example, a patient, who is arranged on a table (not shown) in the examination zone 5, parallel to the direction of the rotational axis R or the z-axis. The motors 7, 8 are controlled by a control unit 9, for instance, such that the x-ray radiation device 2 and the object within the examination zone 5 move relatively to each other along a helical trajectory. However, it is also possible that the object within the examination zone 5 is not moved, but that only the x-ray radiation device 2 is rotated, i.e., that the x-ray radiation device 2 moves along a circular trajectory relative to the object.

During the movement of the x-ray radiation device 2 relative to the object, the detection elements 3 of the photon counting detection device 6 detect the x-ray radiation after having traversed the examination zone 5 and the photon counting detection device 6 measures for each detection element 3 photon counts in one or more energy bins during the detection period. Therefore, the x-ray radiation device 2, the elements for moving the x-ray radiation device 2 relative to the object, in particular, the motors 7, 8 and the support 1, and the photon counting detection device 6 can be regarded as being components of a photon counting x-ray radiation detection system 31.

The spectrally resolving computed tomography system 17, in particular, the photon counting x-ray radiation detection system 31, further comprises a correction unit 12 for estimating for each detection element 3 an amount of a build up charge present in the detection element 3 and for correcting the measured photon counts for the detection element 3 based on the estimated amount of the build up charge. A reconstruction unit 14 reconstructs a computed tomography image based on the corrected photon counts by using known reconstruction algorithms. The reconstruction may be based on, for instance, a filtered back projection technique, an iterative reconstruction technique, a Radon inversion technique, et cetera. The corrected photon counts constitute spectrally resolved projection data and the reconstruction may include a decomposition of the spectrally resolved projection data into different components, which may be related to different materials of the object within the examination zone 5 and/or to different physical effects, and a generation of one or more computed tomography images based on the decomposed spectrally resolved projection data. For instance, a computed tomography image may be reconstructed, which is indicative of a single decomposed component only or of several of the decomposed components. The reconstructed computed tomography image may be shown on a display 16. For decomposing the spectrally resolved projection data into different components, known decomposition algorithms can be used like the algorithm disclosed in J. P. Schlomka et al., "Experimental feasibility of multi-energy photon-counting K-edge imaging in preclinical computed tomography", Physics in Medicine and Biology, Vol. 53, No. 15 (2008), the contents of which are herein incorporated by reference in their entirety. Additionally or alternatively, an image-based material decomposition may also be applied.

The spectrally resolving computed tomography system 17 further comprises an input unit 15 like a computer mouse, a keyboard, a touchpad, et cetera, in order to allow a user to, for instance, input commands like start or stop commands and/or set parameters like acquisition and reconstruction parameters. The control unit 9 may also control the photon counting detection device 6, the correction unit 12, and/or the reconstruction unit 14.

The photon counting detection device 6 preferentially comprises a photon counting detector that makes use of a direct conversion material, such as CdTe, CaZnTe or Si. Such a photon counting detector is known, for instance, from R. Steadman et al., "ChromAIX: Fast photon-counting ASIC for Spectral Computed Tomography", Nuclear Instruments and Methods in Physics Research Section A: Accelerators, Spectrometers, Detectors and Associated Equipment, Vol. 648, Suppl. 1 (2011), the contents of which are herein incorporated by reference in their entirety.

In this embodiment, the correction unit 12 is adapted to perform the estimating and the correcting for the detection element 3 based on a mathematical correction model having a plurality of model parameters, wherein the correction model models the amount of the build up charge in dependence of time and relates it to correction values for correcting the measured photon count in each energy bin. The correction model can be described in more detail based on the following equations:

$$m_b^P(t, \overline{M}) = m_b^P(t=0, \overline{M}) + \gamma_b^P(\overline{M}) Q^P(t) \qquad (1)$$

$$\frac{d}{dt} Q^P(t) = S^P(t, \overline{M}) - \alpha^P Q^P(t) \qquad (2)$$

$$Q^P(t) = \left[ Q^P(t=0) + \int_0^t S^P(t, \overline{M}) e^{\alpha^P t} dt \right] e^{-\alpha^P t} \qquad (3)$$

Equation (1) specifies that the photon count $m_b^P(t, \vec{M})$ measured for the detection element P in the energy bin b at a given point in time t depends on the material combination $\vec{M}$ of the object on a path of the x-ray radiation 4 from the x-ray radiation device 6 to the detection element P. This measured photon count is modeled as a correct photon count $m_b^P(t=0, \vec{M})$ that would be measured at a point in time t=0 at which the detection element P has not yet been illuminated during the scan reduced by an error value $\gamma_b^P(\vec{M})Q^P(t)$ that is caused by the build up charge $Q^P(t)$ that is present in the detection element P at the given point in time t.

The modeling of the amount of the build up charge $Q^P(t)$ in dependence of time t is given by equation (2). It comprises an increase component and a decrease component which respectively model an increase and a decrease of the amount of the build up charge $Q^P(t)$ in dependence of time t.

More specifically, the increase component depends on a first model parameter $S^P(t, \vec{M})$ which depends on the x-ray radiation 4 and on a material combination $\vec{M}$ of the object on a path of the x-ray radiation 4 from the x-ray radiation device 2 to the detection element P. In essence, the first model parameter $S^P(t, \vec{M})$ describes the spectral distribution of the x-ray radiation 4 that ultimately illuminates the detection element P.

The decrease component depends on a second model parameter $\alpha^P$ which defines a constant decrease rate of the amount of the build up charge $Q^P(t)$. The second model parameter $\alpha^P$ accounts for the decrease of the amount of the build up charge due to trapped charges becoming untrapped, e.g., through acoustic phonons, over time, while the state of the material comprised by the detection element relaxes towards an equilibrium state.

If the first model parameter $S^P(t, \vec{M})$ and the second model parameter $\alpha^P$ are known, the amount of the build up charge $Q^P(t)$ at the given point in time t can be estimated by means of equation (3).

The negative of the error value $\gamma_b^P(\vec{M})Q^P(t)$ in equation (1) is then preferably used as the correction value for the energy bin b. With this, it can be seen that the amount of the build up charge $Q^P(t)$ is related to the correction values by a third model parameter $\gamma_b^P(\vec{M})$ which is specific for each energy bin b and which is based on a material combination $\vec{M}$ of the object on a path of the x-ray radiation 4 from the x-ray radiation device 2 to the detection element P.

Based on the above equations (1) to (3), the photon counts $m_b^P(\Delta t\, n)$ measured by the detection element P in the energy bin b during the detection period n, wherein $\Delta t$ specifies the length of the detection periods, can then be corrected based on the following equations:

$$\tilde{m}_b^P(\Delta t n) = m_b^P(\Delta t n) - \gamma_b^P(\vec{M}_n) Q^P(\Delta t n) \quad (4)$$

$$Q^P(\Delta t n) = [\Sigma_{j=1}^n S^P(\Delta t j, \vec{M}_j) e^{\alpha^P \Delta t j} \Delta t] e^{-\alpha^P \Delta t n} \quad (5)$$

Herein, $\tilde{m}_b^P(\Delta t\, n)$ denotes the corrected photon counts for the detection element P in the energy bin b during the detection period n. Equation (5) models the amount of the build up charge $Q^P(\Delta t\, n)$ present in the detection element P during the detection period n based on a summation of amounts of the charge build up (including its decay by de-trapping) during detection periods $j=1 \ldots n$ of the scan, wherein the summation begins at a first detection period $j=1$ of the scan. Here, the amount of the build up charge $Q^P(\Delta t\, j)$ is modeled to be to be equal to a predetermined value, in particular, zero, at the beginning of the first detection period $j=1$ of the scan. With the amount of the build up charge $Q^P(\Delta t\, n)$ present in the detection element P during the detection period n estimated according to equation (5), the correction can then be performed according to equation (4), wherein $m_b^P(\Delta t\, n)$ denotes the measured photon counts for the detection element P in the energy bin b during the detection period n and $\gamma_b^P(\vec{M}_n) Q^P(\Delta t\, n)$ denotes the correction value for each energy bin b.

In order to determine the model parameters $S^P(t, \vec{M})$, $\alpha^P$ and $\gamma_b^P(\vec{M})$ for each detection element P and each energy bin b, a suitable calibration is used in this embodiment. To this end, the spectrally resolving computed tomography system 17, in particular, the photon counting x-ray radiation detection system 31, further comprises a model parameter determining unit 13 for determining for each detection element 3 the model parameters of the correction model based on calibration photon counts measured for the detection element 3 in the one or more energy bins b during a plurality of detection periods of one or more calibration scans, during which a calibration phantom is used as the object.

Here, the calibration photon counts for the detection element 3 comprise calibration photon counts for different material combinations of the calibration phantom, wherein the model parameter determining unit 13 is adapted to determine the model parameters $S^P(t, \vec{M})$, $\alpha^P$ and $\gamma_b^P(\vec{M})$ for the detection element 3 for each of the different material combinations.

Figure 2:
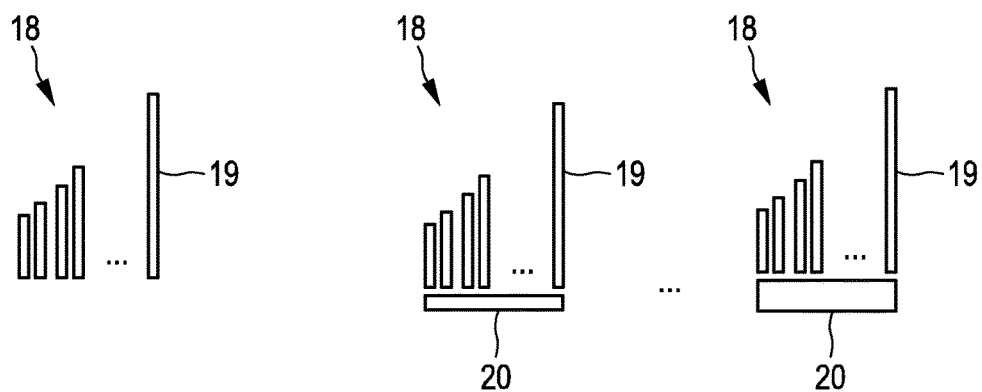
FIG. 2 shows schematically and exemplarily a calibration phantom that can be used in the calibration of the x-ray imaging system.

A suitable calibration phantom that can be used in the calibration of the spectrally resolving computed tomography system 17 is schematically and exemplarily shown in FIG. 2. As can be seen from this figure, the calibration phantom 18 can preferentially comprise several slabs with accurately known dimensions and made of materials whose chemical composition spans the range of atomic numbers of materials expected in the object, such as a human or an animal. For instance, the calibration phantom can comprise a water equivalent material 19, such as Delrin, only or it can comprise at least one further material 20, for instance, a bone equivalent material, such as aluminum, and/or a contrast agent equivalent material, such as iodine. The maximum lengths of the slabs are preferably chosen to span the expected attenuation of the object. The calibration phantom 18 can be placed between the x-ray radiation device 2 and the photon counting detection device 6 and measurements can be made using the same type of scan, e.g. the same scan protocol, as used when scanning the object. The support 1 (gantry) can be fixed to make measurements of the calibration phantom 18. In order to allow the calibration of each detection element 3, it is preferred that the slabs of the calibration phantom 18 are constructed wide enough to be simultaneously placed between the x-ray radiation device 2 and each detection element 3 of the photon counting detection device 6. From the known geometry of the x-ray radiation device 2, in particular, the shape of the provided x-ray radiation beam 4, and the photon counting detection device 6, together with the known dimensions and placement of the slabs of the calibration phantom 18, the respective material lengths, i.e., the lengths traversed by the x-ray radiation 4 through a respective material from the x-ray radiation device 2 to each of the detection elements 3 can then be determined.

Figure 3:
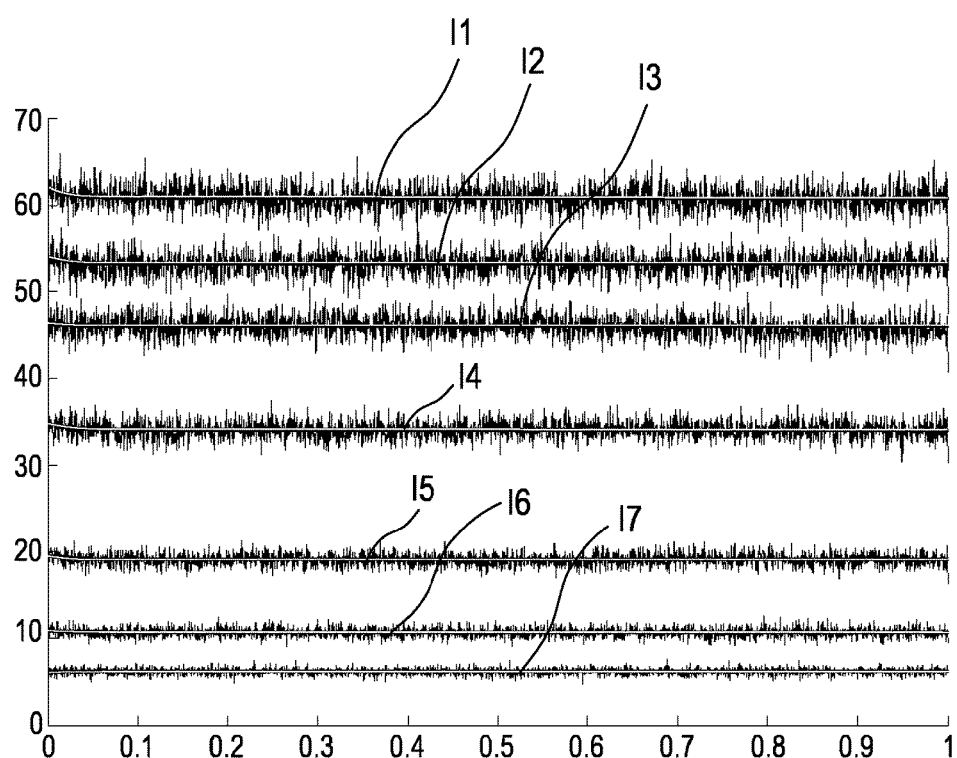
FIG. 3 shows schematically and exemplarily some results of fitting the correction model to calibration photon counts measured during a plurality of detection periods of a calibration scan.

In this embodiment, the model parameter determining unit 13 is adapted to determine the model parameters $S^P(t, \vec{M})$, $\alpha^P$ and $\gamma_b^P(\vec{M})$ for the detection element 3 by fitting the correction model to the calibration photon counts. Some results of fitting the correction model to calibration photon counts measured during a plurality of detection periods of a calibration are schematically and exemplarily shown in FIG. 3. In the figure, the horizontal axis indicates the time in seconds—and, therewith, the detection periods—and the vertical axis indicates the measured calibration photon counts. The seven graphs correspond to measurements with a calibration phantom 18 with seven different lengths of water equivalent material, here, Delrin, for a single detection element 3 in one particular energy bin b. The highest photon counts correspond to the shortest Delrin length and the lowest photon counts correspond to the longest Delrin length. As can be seen, the fitted correction model (represented by fitting curves 11 to 17) matches the measured photon counts for each of the seven Delrin lengths quite well. The fitting procedure, in this example, was based on a multi-dimensional non-linear fitting routine, which minimizes a chi-square merit function. As a result of the calibration procedure, the model parameters $S^P(t, \vec{M})$, $\alpha^P$ and $\gamma_b^P(\vec{M})$ are available for each detection element 3 and for the different material combinations of the calibration phantom 18.

Figure 4:
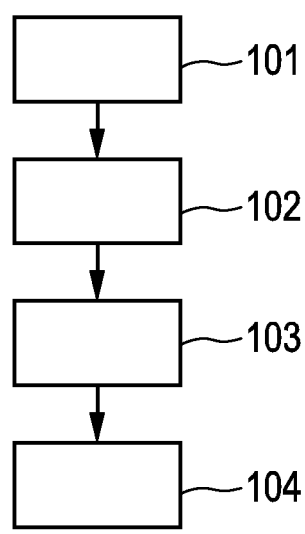
FIG. 4 shows a flowchart exemplarily illustrating an embodiment of an x-ray imaging method.

In the following, an embodiment of an x-ray imaging method will exemplarily be described with reference to a flowchart shown in FIG. 4. In this example, the imaging method is a spectrally resolving computed tomography method that can be performed with the spectrally resolving computed tomography system 17 described with reference to FIG. 1 above.

In step 101, polychromatic x-ray radiation 4, which traverses the examination zone 5 during a detection period of a scan, is provided by the x-ray radiation device 2 and the x-ray radiation is detected after having traversed the examination zone 5, by the photon counting detection device 6 comprising the detection elements 3, while the x-ray radiation device 2 rotates around an object, which is accommodated in the examination zone 5. Also in step 101, the photon counting detection device 6 measures for each detection element 3 photon counts in one or more energy bins during the detection period. In step 102, for each detection element 3, an amount of a build up charge present in the detection element 3 is estimated and the measured photon counts for the detection element 3 are corrected based on the estimated amount of the build up charge, by the correction unit 12. In step 103, the corrected photon counts are used by the reconstruction unit 14 for reconstructing a computed tomography image and in step 104, the reconstructed computed tomography image is shown on the display 16.

Steps 101 and 102 can also be regarded as being steps of a photon counting x-ray radiation detection method. Moreover, the method can comprise further steps like the determination for each detection element 3 of the model parameters of the correction model.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage. Procedures like the estimation for each detection element of the amount of the build up charge present in the detection element, the correction of the measured photon counts for the detection element, the determination for each detection element of the model parameters of the correction model, the reconstruction of the image, et cetera, performed by one or several units or devices can be performed by any other number of units or devices. These operations and/or the control of the x-ray imaging system in accordance with the x-ray imaging method and/or the control of the photon counting x-ray radiation detection system in accordance with the photon counting x-ray radiation detection method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a photon counting x-ray radiation detection system. The system comprises an x-ray radiation device for providing polychromatic x-ray radiation for traversing an examination zone during a detection period of a scan, wherein the examination zone is adapted to accommodate an object. A photon counting detection device comprising detection elements detects the x-ray radiation after having traversed the examination zone and measures for each detection element photon counts in one or more energy bins during the detection period. A correction unit estimates for each detection element an amount of a build up charge present in the detection element and corrects the measured photon counts for the detection element based on the estimated amount of the build up charge. This allows the corruption of the photon count rates caused by the build up charges to be compensated and to improve the determination of the photon counts.

The invention claimed is:

1. A photon counting x-ray radiation detection system, the system comprising:
    an x-ray radiation device for providing polychromatic x-ray radiation for traversing an examination zone during a detection period of a scan, wherein the examination zone is adapted to accommodate an object,
    a photon counting detection device comprising detection elements for detecting the x-ray radiation after having traversed the examination zone, wherein the photon counting detection device is adapted to measure for each detection element photon counts in one or more energy bins during the detection period, and
    a correction unit for estimating for each detection element an amount of a build up charge present in the detection element and for correcting the measured photon counts for the detection element based on the estimated amount of the build up charge.

2. The photon counting x-ray radiation detection system as defined in claim 1, wherein the correction unit is adapted to perform the estimating and the correcting for the detection element based on a mathematical correction model having a plurality of model parameters, wherein the correction model models the amount of the build up charge in dependence of time and relates it to correction values for correcting the measured photon count in each energy bin.

3. The photon counting x-ray radiation detection system as defined in claim 2, wherein the modeling of the amount of the build up charge in dependence of time comprises an increase component and a decrease component which respectively model an increase and a decrease of the amount of the build up charge in dependence of time.

4. The photon counting x-ray radiation detection system as defined in claim 3, wherein the increase component depends on a first model parameter which depends on the x-ray radiation and on a material combination of the object on a path of the x-ray radiation from the x-ray radiation device to the detection element.

5. The photon counting x-ray radiation detection system as defined in claim 3, wherein the decrease component depends on a second model parameter which defines a constant decrease rate of the amount of the build up charge.

6. The photon counting x-ray radiation detection system as defined in claim 2, wherein the amount of the build up charge is related to the correction values by a third model parameter which is specific for each energy bin and which is based on a material combination of the object on a path of the x-ray radiation from the x-ray radiation device to the detection element.

7. The photon counting x-ray radiation detection system as defined in claim 2, wherein the modeling of the amount of the build up charge in dependence of time is based on an integration or a summation of amounts of the charge build up during previous detection periods of the scan.

8. The photon counting x-ray radiation detection system as defined in claim 7, wherein the integration or summation begins at a first detection period of the scan.

9. The photon counting x-ray radiation detection system as defined in claim 8, wherein the amount of the build up charge is modeled to be equal to a predetermined value, in particular, zero, at the beginning of the first detection period of the scan.

10. The photon counting x-ray radiation detection system as defined in claim 2, further comprising:

a model parameter determining unit for determining for each detection element the model parameters of the correction model based on calibration photon counts measured for the detection element in the one or more energy bins during a plurality of detection periods of one or more calibration scans, during which a calibration phantom is used as the object.

11. The photon counting x-ray radiation detection system as defined in claim 10, wherein the calibration photon counts for the detection element comprise calibration photon counts for different material combinations of the calibration phantom, wherein the model parameter determining unit is adapted to determine the model parameters for the detection element for each of the different material combinations.

12. The photon counting x-ray radiation detection system as defined in claim 10, wherein the model parameter determining unit is adapted to determine the model parameters for the detection element by fitting the correction model to the calibration photon counts.

13. An x-ray imaging system, comprising:
a photon counting x-ray radiation detection system as defined in claim 1, and
a reconstruction unit for reconstructing an image based on the corrected photon counts.

14. A photon counting x-ray radiation detection method, the method comprising:
providing polychromatic x-ray radiation for traversing an examination zone during a detection period of a scan, by an x-ray radiation device, wherein the examination zone is adapted to accommodate an object,
detecting the x-ray radiation after having traversed the examination zone, by a photon counting detection device comprising detection elements, wherein the photon counting detection device measures for each detection element photon counts in one or more energy bins during the detection period, and
estimating for each detection element an amount of a build up charge present in the detection element and correcting the measured photon counts for the detection element based on the estimated amount of the build up charge, by a correction unit.

* * * * *